(12) United States Patent
Yu et al.

(10) Patent No.: US 6,936,045 B2
(45) Date of Patent: *Aug. 30, 2005

(54) MALLEABLE CRYOSURGICAL PROBE

(75) Inventors: Xiaoyu Yu, San Diego, CA (US); Jay J. Eum, Irvine, CA (US); David J. Battles, Laguna Beach, CA (US)

(73) Assignee: Endocare, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/957,337

(22) Filed: Sep. 20, 2001

(65) Prior Publication Data
US 2003/0055415 A1 Mar. 20, 2003

(51) Int. Cl.⁷ ............................................. A61B 18/02
(52) U.S. Cl. ...................................... 606/23; 606/20
(58) Field of Search ..................... 606/20–26; 607/104, 607/105, 107

(56) References Cited

U.S. PATENT DOCUMENTS

| | | | |
|---|---|---|---|
| 3,800,552 A | 4/1974 | Sollami | 62/293 |
| 3,913,581 A | 10/1975 | Ritson | 128/303.1 |
| 4,072,152 A | 2/1978 | Linehan | |
| 4,082,096 A * | 4/1978 | Benson | 128/303.1 |
| 5,108,390 A | 4/1992 | Potocky | 606/21 |
| 5,388,415 A | 2/1995 | Glinks | 62/51.2 |
| 5,452,582 A | 9/1995 | Longsworth | 62/51.2 |
| 5,522,870 A | 6/1996 | BenZion | 607/104 |
| 5,759,182 A | 6/1998 | Varney et al. | 606/21 |
| 5,800,487 A | 9/1998 | Mikus | 607/105 |
| 5,899,899 A | 5/1999 | Arless | 606/22 |
| 5,906,612 A * | 5/1999 | Chinn | 606/20 |
| 6,039,730 A * | 3/2000 | Rabin et al. | 606/23 |
| 6,074,412 A | 6/2000 | Mikus | 607/105 |
| 6,161,543 A | 12/2000 | Cox | 128/898 |
| 6,241,722 B1 * | 6/2001 | Dobak et al. | 606/23 |
| 6,270,476 B1 * | 8/2001 | Santoianni et al. | 604/95.04 |
| 6,464,716 B1 * | 10/2002 | Dobak, III et al. | 607/105 |
| 6,497,703 B1 * | 12/2002 | Korteling et al. | 606/23 |
| 2003/0055416 A1 | 3/2003 | Damasco et al. | 606/21 |

OTHER PUBLICATIONS

Walker & Gingham, Low Capacity Cryogenic Refrigeration, pp. 67 ET SEQ (1994).

* cited by examiner

Primary Examiner—Michael Peffley
Assistant Examiner—Aaron Roane
(74) Attorney, Agent, or Firm—Lawrence N. Ginsberg

(57) ABSTRACT

The malleable cryosurgical probe includes a cryostat assembly and a cryoprobe assembly. The cryostat assembly includes an elongated shaft assembly having at least one malleable segment thereof and a closed distal end. The shaft assembly includes at least one freezing portion, at least one thermally insulated portion and a thermally insulating element positioned about the thermally insulated portion. A cryostat is operably associated with the elongated shaft assembly. It includes a cryostat inlet for receiving gas entering the cryostat, a cryostat outlet and a heat exchanger positioned between the cryostat outlet and the cryostat inlet. The heat exchanger receives gas from the cryostat inlet and provides heat transfer between gas flowing within the cryostat and fluid exterior thereto. At least one Joule-Thomson nozzle is in fluid communication with the cryostat outlet. The at least one Joule-Thomson nozzle expands gas expelled therefrom. The expanded cold fluid communicates with the freezing portion to provide cooling thereof. The cryoprobe assembly includes a handle assembly for supporting the cryostat assembly and a fluid supply line assembly connectable to a fluid source at one end and to the cryostat inlet at a second end. The heat exchanger is positioned at a location longitudinally spaced from the freezing portion(s).

24 Claims, 7 Drawing Sheets

MALLEABLE CRYOSURGICAL PROBE

BACKGROUND OF THE INVENTION

1. Field of the Invention

This invention relates to cryosurgical probes and more particularly to a cryosurgical probe that is malleable for use with applications in which a desired angle of entry and contact with the patient's organ is required.

2. Description of the Related Art

Cryosurgical probes are used to treat a variety of diseases. The cryosurgical probes quickly freeze diseased body tissue, causing the tissue to die after which it will either be absorbed by the body, expelled by the body, sloughed off or replaced by scar tissue. Cryothermal treatment is currently used to treat prostate cancer and benign prostate disease, breast tumors including breast cancer, liver tumors including cancer, glaucoma and other eye diseases. Cryosurgery may also be used for the treatment of a number of other diseases and conditions including the treatment of cardiac arrhythmias, such as atrial fibrillation.

A variety of cryosurgical instruments, variously referred to as cryoprobes, cryosurgical probes, cryosurgical ablation devices, and cryostats and cryocoolers, have been available for cryosurgery. These devices typically use the principle of Joule-Thomson expansion to generate cooling. They take advantage of the fact that most fluids, when rapidly expanded, become extremely cold. In these devices, a high pressure gas such as argon or nitrogen is expanded through a nozzle inside a small cylindrical shaft or sheath typically made of steel, and the Joule-Thomson expansion cools the steel sheath to a cold temperature very rapidly.

An exemplary device is illustrated in Sollami, Cryogenic Surgical Instrument, U.S. Pat. No. 3,800,552 (Apr. 2, 1974). Sollami shows a basic Joule-Thomson probe with a sheath made of metal, a fin-tube helical gas supply line leading into a Joule Thomson nozzle which directs expanding gas into the probe. Expanded gas is exhausted over the fin-tube helical gas supply line, and pre-cools incoming high pressure gas. For this reason, the coiled supply line is referred to as a heat exchanger, and is beneficial because, by pre-cooling incoming gas, it allows the probe to obtain lower temperatures.

Ben-Zion, Fast Changing Heating and Cooling Device and Method, U.S. Pat. No. 5,522,870 (Jun. 4, 1996) applies the general concepts of Joule-Thomson devices to a device that is used first to freeze tissue and then to thaw the tissue with a heating cycle. Nitrogen is supplied to a Joule-Thomson nozzle for the cooling cycle, and helium is supplied to the same Joule-Thomson nozzle for the warming cycle. Preheating of the helium is presented as an essential part of the invention, necessary to provide warming to a sufficiently high temperature.

A Joule-Thomson cryostat for use as a gas tester is illustrated in Glinka, System for a Cooler and Gas Purity Tester, U.S. Pat. No. 5,388,415 (Feb. 14, 1995). Glinka also discloses use of the by-pass from the Joule-Thomson Nozzle to allow for cleaning the supply line, and also mentions that the high flow of gas in the by-pass mode will warm the probe. This is referred to as mass flow warming, because the warming effect is accomplished purely by conduction and convection of heat to the fluid mass flowing through the probe.

Various cryocoolers use mass flow warming, flushed backwards through the probe, to warm the probe after a cooling cycle. Lamb, Refrigerated Surgical Probe, U.S. Pat. No. 3,913,581 (Aug. 27, 1968) is one such probe, and includes a supply line for high pressure gas to a Joule-Thomson expansion nozzle and a second supply line for the same gas to be supplied without passing through a Joule-Thomson nozzle, thus warming the catheter with mass flow. Longsworth, Cryoprobe, U.S. Pat. No. 5,452,582 (Sep. 26, 1995) discloses a cryoprobe which uses the typical fin-tube helical coil heat exchanger in the high pressure gas supply line to the Joule-Thomson nozzle. The Longsworth cryoprobe has a second inlet in the probe for a warming fluid, and accomplishes warming with mass flow of gas supplied at about 100 psi. The heat exchanger, capillary tube and second inlet tube appear to be identical to the cryostats previously sold by Carleton Technologies, Inc. of Orchard Park, N.Y.

Each of the above mentioned cryosurgical probes builds upon prior art which clearly establishes the use of Joule-Thomson cryocoolers, heat exchangers, thermocouples, and other elements of cryocoolers. Walker, *Miniature Refrigerators for Cryogenic Sensor and Cold Electronics* (1989) (Chapter 2) and Walker & gingham, *Low Capacity Cryogenic Refrigeration*, pp. 67 et seq. (1994) show the basic construction of Joule-Thomson cryocoolers including all of these elements. The Giaque-Hampson heat exchanger, characterized by coiled finned-tube, transverse flow recuperative heat exchanger is typical of cryocoolers. The open mandrel around which the finned tube coil is placed is also typical of cryocoolers.

U.S. Pat. Nos. 5,800,487 and 6,074,412, both entitled Cryoprobe, issued to Mikus et and assigned to the present assignee disclose cryoprobes using Joule-Thomson nozzles and finned tube helical coil heat exchangers.

Cryosurgical probes may be used, as mentioned above, to treat diseases of the prostate, liver, and breast, and they have gynecological applications as well. The cryosurgical probes form iceballs which freeze disease tissue. Each application has a preferred shape of iceball, which, if capable of production, would allow cryoablation of the diseases tissue without undue destruction of surrounding healthy tissue. For example, prostate cryoablation optimally destroys the lobes of the prostate, while leaving the surrounding neurovascular bundles, bladder neck sphincter and external sphincter undamaged. The prostate is wider at the base and narrow at the apex. A pear or fig shaped ice ball is best for this application. Breast tumors tend to be small and spherical, and spherical iceballs will be optimal to destroy the tumors without destroying surrounding breast tissue. Liver tumors may be larger and of a variety of shapes, including spherical, olive shaped, hot dog shaped or irregularly shaped, and may require more elongated iceballs, larger iceballs, and iceballs of various shapes.

During open chest surgery transmural cryo-lesions can be created on or in the heart to treat cardiac arrhythmia (including atrial fibrillation). A suitable cryoprobe would be useful for this application. Due to the nature of the procedure and anatomical locations that lesions must be placed, the cryoprobe must be sufficiently malleable by the surgeon to be placed on the heart surface but stiff enough such that pressure can be applied without flexing the shaft.

The prior art includes references to malleable and flexible cryoprobes. For example, U.S. Pat. No. 6,161,543, issued to Cox et al discloses the use of a malleable probe. The probe has a malleable shaft. A malleable metal rod is coextruded with a polymer to form the shaft. The rod permits the user to shape the shaft as necessary so that a tip can reach the tissue to be ablated.

U.S. Pat. No. 5,108,390, issued to Potocky et al discloses a highly flexible cryoprobe that can be passed through a blood vessel and into the heart without external guidance other than the blood vessel itself.

SUMMARY

The present invention is a malleable cryosurgical probe. It includes a cryostat assembly and a cryoprobe assembly. The cryostat assembly includes an elongated shaft assembly having at least one malleable segment thereof and a closed distal end. The shaft assembly includes at least one freezing portion, at least one thermally insulated portion and a thermally insulating element positioned about the thermally insulated portion. A cryostat is operably associated with the elongated shaft assembly. It includes a cryostat inlet for receiving gas entering the cryostat, a cryostat outlet and a heat exchanger positioned between the cryostat outlet and the cryostat inlet. The heat exchanger receives gas from the cryostat inlet and provides heat transfer between gas flowing within the cryostat and fluid exterior thereto. At least one Joule-Thomson nozzle is in fluid communication with the cryostat outlet. The at least one Joule-Thomson nozzle expands gas expelled therefrom. The expanded cold fluid communicates with the freezing portion to provide cooling thereof. The cryoprobe assembly includes a handle assembly for supporting the cryostat assembly and a fluid supply line assembly connectable to a fluid source at one end and to the cryostat inlet at a second end. The heat exchanger is positioned at a location longitudinally spaced from the freezing portion(s).

Positioning of the heat exchanger in a position longitudinally spaced from the freezing portion(s) provides the capability of providing malleable segments. The heat exchanger can be made relatively large and powerful providing enhanced operation while concomitantly providing for a freezing portion and/or thermally insulated portion of the elongated shaft assembly that has a small diameter. The malleable segments are formed of material that permits reshaping and bending of the elongated shaft assembly as a unit to reposition the ablating surface for greater ablation precision. Moreover, enhancements are disclosed for assuring that there can be bending and reshaping without kinking or collapsing. Such properties are especially imperative for such devices employed in the formation of transmural lesions in anatomical locations that are particularly difficult to access. The malleable segment is sufficiently malleable to be fashioned to the desired shape while rigid enough to retain the shape during clinical use.

Other objects, advantages, and novel features will become apparent from the following detailed description of the invention when considered in conjunction with the accompanying drawings.

DETAILED DESCRIPTION OF THE INVENTION

Figure 1:
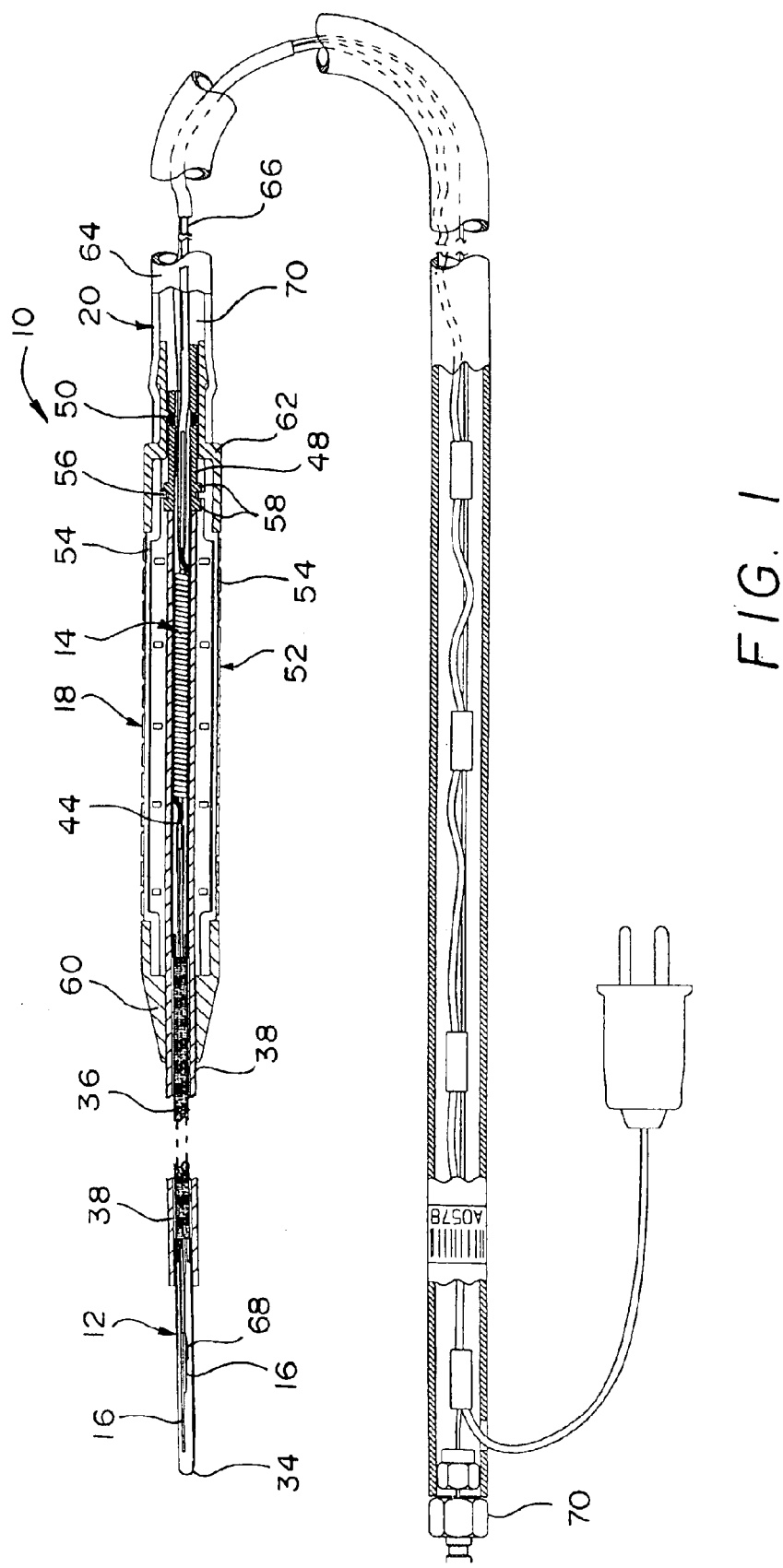
FIG. 1 is a crossectional view of a preferred embodiment of the malleable cryosurgical probe of the present invention.
Figure 2:
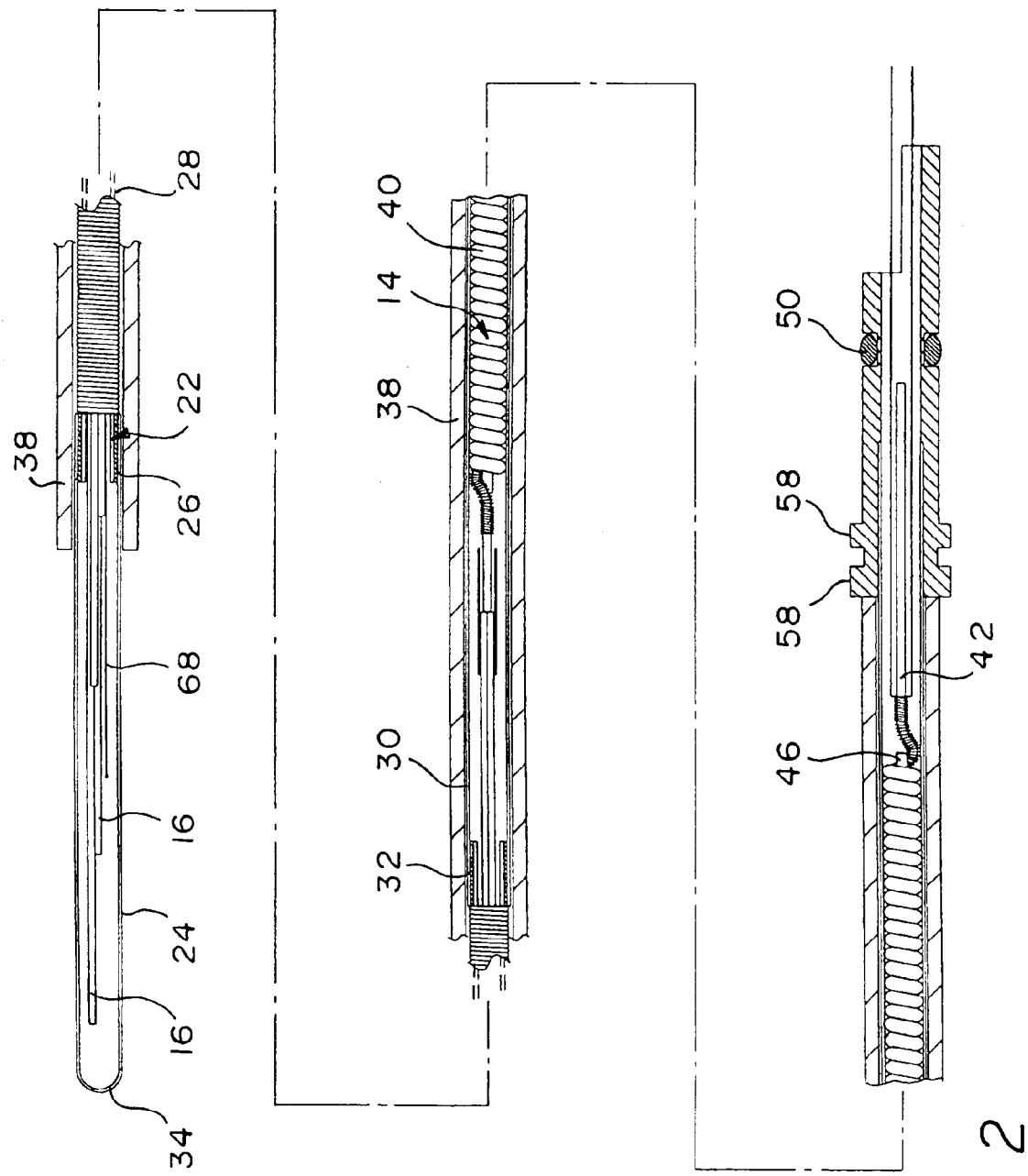
FIG. 2 is an enlarged view of the cryostat assembly of the malleable cryosurgical probe of FIG. 1 with the handle removed for the purposes of clarity.

Referring to the drawings and the characters of reference marked thereon FIGS. 1 and 2 illustrate a preferred embodiment of the present invention, designated generally as 10. The malleable cryosurgical probe 10 includes a cryostat assembly and a cryoprobe assembly. The cryostat assembly includes an elongated shaft assembly designated generally as 12, a cryostat designated generally as 14, and Joule-Thomson nozzles 16. The cryoprobe assembly includes a handle assembly, designated generally as 18 and a fluid supply line assembly 20.

The elongated shaft assembly 12 includes a main body portion 22 and a tip portion 24 welded thereto with a spacer 26. The main body portion 22 includes a thermally protected malleable segment 28 and an adapter segment 30, these two segments being welded together with a spacer 32. The thermally protected malleable segment 28 is positioned between the adapter segment 30 and the other malleable segment, i.e. the tip portion 24. The tip portion 24 has a closed distal end 34 and is also malleable. Both the main body portion 22 and the tip portion 24 are tubular elements. They may be formed of, for example, annealed metals such as annealed stainless steel, annealed nickel or annealed copper. The elongated shaft assembly may have a wide range of lengths depending on the desired purpose, i.e. it might be one to perhaps twenty inches long. The outer diameter may be in a range of between about 0.04 and 0.5 inches.

A shaft enhancement element such as a spring coil member 36 is positioned about the tube of the thermally protected malleable segment 28. The spring coil member 36 enhances the capability of the thermally protected malleable segment 28 of bending and reshaping without kinking or collapsing.

The elongated shaft assembly includes a thermally insulating element 38 positioned over the main body portion 22 to define a thermally insulated portion. The portion of the tip portion 24 that remains uncovered defines a freezing portion. The freezing portion is preferably made of a thermally conductive material, such as stainless steel, as noted above. The elongated shaft assembly 12 has been shown with three different parts, i.e. malleable segment 28, adapter segment 30 and tip portion 24. This is to accommodate various desired sizes of tip portions 24. However, use of these three parts has been shown by way of illustration and not limitation. For example, a one-piece shaft can be utilized. The malleable segment preferably has a minimum bend radius of about 0.25 inches. The freezing portion typically has an outer diameter in a range between about 0.04 inches and about 0.5 inches. The thermally insulated portion typically has an outer diameter in a range of between about 0.04 inches and about 0.50 inches, preferably in a range of about 0.10 inches and about 0.15 inches.

The cryostat 14 comprises a coiled heat exchanger 40. A cryostat inlet 42 receives gas entering the cryostat while a cryostat outlet 44 provides the gas to the Joule-Thomson nozzles 16. The coiled heat exchanger 40 is coiled around a mandrel 46. In between each winding of the heat exchanger, gaps are formed between the coil and the main body portion 22, and gaps are formed between the coil and the mandrel 46. This construction is known as a Giaque-Hampson heat exchanger. The heat exchanger, which is an integral part of the high pressure gas pathway, is made with finned tubing, with numerous fins throughout its length.

The handle assembly 18 includes an anchor 48 securely connected to the cryostat assembly by welding or other conventional means. An o-ring 50 prevents fluid from escaping through the handle assembly 18. A handle, designated generally as 52, includes two elongated opposing handle body elements 54 with radially inward extensions 56 for engaging the space between radially outward extensions 58 of the anchor 48. A handle nozzle 60 fits over and secures the handle body elements 54 together at first ends thereof via a friction fit. A handle barb 62 secures the handle body elements 54 together at second ends thereof.

The fluid supply line assembly 20 includes a housing 64 that supports a fluid supply line 66. A temperature measurement device, i.e. a thermocouple 68, is positioned within the elongated shaft assembly, extends through the fluid supply line assembly 20 and is connectable to a data acquisition system. The thermocouple 68 is used to measure and monitor the temperature inside the cryosurgical probe.

Fluid flow through the cryosurgical probe is as follows. High pressure fluid, preferably gaseous argon, and preferably at a pressure of about 3000 psi, is supplied to the assembly through high pressure fitting 70, flows through gas supply line 66, through cryostat inlet 42, into heat exchanger 40, through cryostat outlet 44 and Joule-Thomson nozzles 16. The high pressure gas expands within the expansion chamber and cools to cryogenic temperatures. Condensation of the gas is preferably avoided but can be tolerated. After expanding, the gas is at lower pressure and exhausts over the exhaust gas pathway that includes flow over outside of the coils of the heat exchanger 40. Because it is now cold, it cools the gas flowing inside the coils. This makes cooling more efficient and achieves colder temperatures. After passing through the heat exchanger, the exhaust gas flows through the remainder of the exhaust gas pathway, as indicated by numeral designation 70. The exhaust gas is eventually vented to the atmosphere.

Prior art warming methods such as exhaust blocking, reverse flow heat transfer, and electrical heating can be employed. The preferred method of warming is to supply high pressure helium gas through the supply line, heat exchanger and Joule-Thomson nozzle. Helium gas heats up when expanded through the gas outlet. Thus, the supply of gas to the probe can be switched from high pressure nitrogen or argon to high pressure helium to effect rapid re-warming of the cryosurgical probe.

Figure 3:
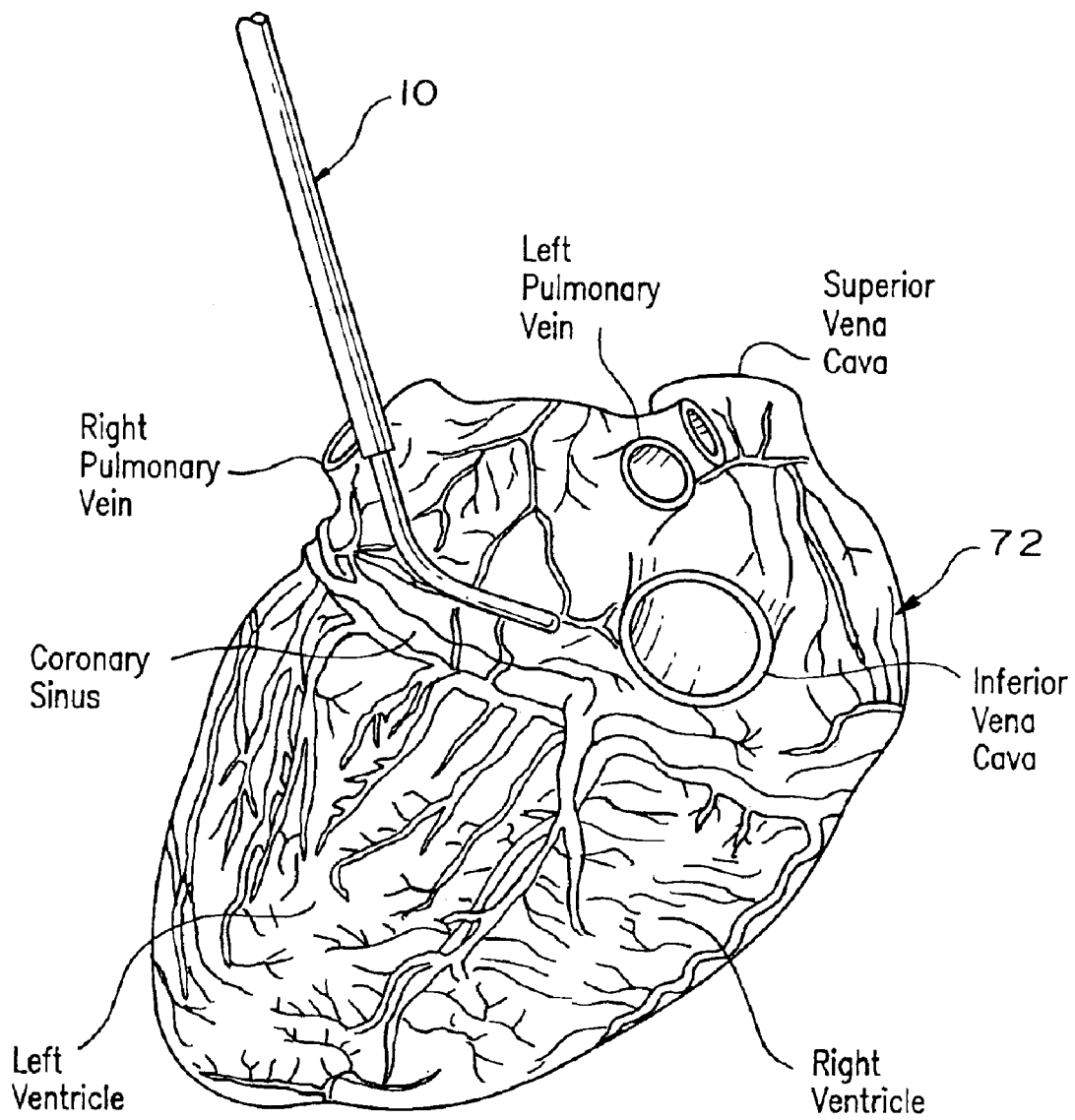
FIG. 3 is a schematic view of the heart with the malleable cryosurgical probe of the present invention shown positioned thereagainst for the treatment of arrhythmias.

Referring now to FIG. 3 the utilization of the present cryosurgical probe 10, positioned against the heart 72, for treating arrhythmias, is illustrated. This creates transmural lesions which have the effect of channeling, limiting or blocking electrical transmissions. Its malleable characteristics allow the cryosurgical probe 10 to create elongated homogenous lesions (either curved or straight) at desired locations which are often difficult to access with a straight surgical implement.

Figure 4:
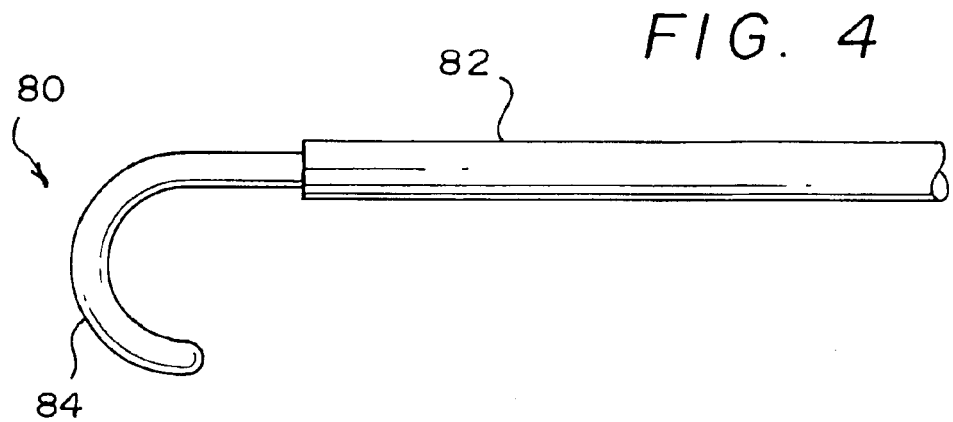
FIG. 4 is a schematic illustration of an embodiment of the cryosurgical probe having a rigid, thermally insulated main portion and a malleable tip portion.

Referring now to FIG. 4 another embodiment of the present invention is illustrated, designated generally as 80. The cryosurgical probe 80 includes an elongated shaft assembly having a rigid, thermally insulated main portion 82 with the malleable segment being a tip portion 84. This embodiment is generally useful when the surgeon requires a rigid shaft.

Figure 5:
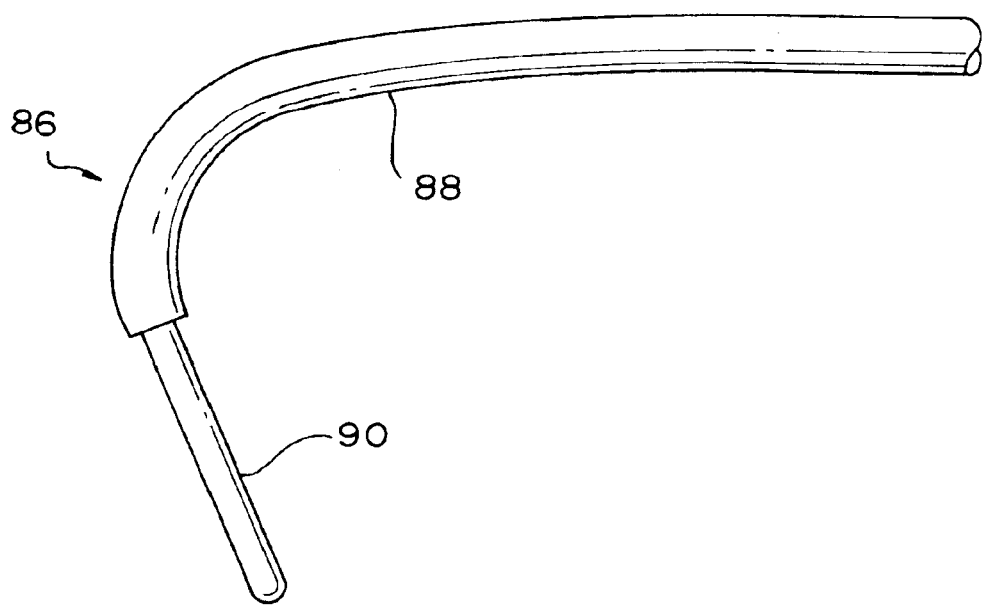
FIG. 5 is a schematic illustration of an embodiment of the cryosurgical probe having a malleable, thermally insulated main portion and a rigid tip portion.

Referring now to FIG. 5 another embodiment of the present invention is illustrated, designated generally as 86. The cryosurgical probe 86 includes an elongated shaft assembly having a malleable, thermally insulated main portion 88 with the tip portion 90 being rigid.

Figure 6:
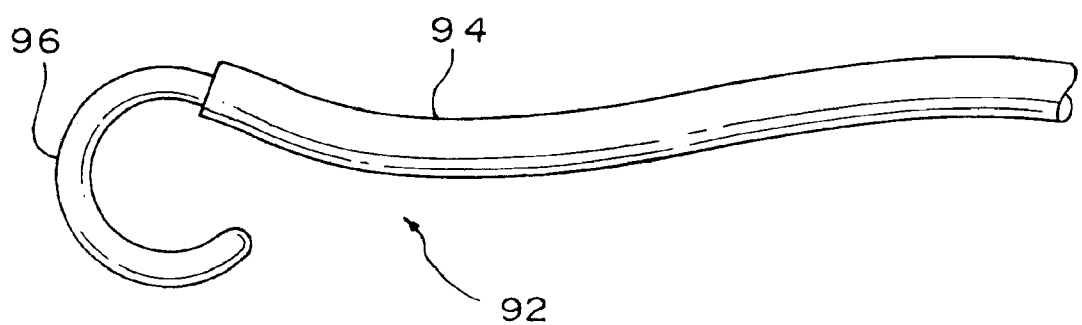
FIG. 6 is a schematic illustration of an embodiment of the cryosurgical probe having a malleable, thermally insulated main portion and a malleable tip portion.

Referring now to FIG. 6 an embodiment of the present invention is illustrated, designated generally as 92 that includes an elongated shaft assembly having a malleable, thermally insulated main portion 94 with the tip portion 96 also being malleable as in the FIG. 1 embodiment. This shows how both the freezing tip portion 96 and the thermally insulated main portion 94 may be malleable. However, for certain applications they may be malleable to different degrees.

Figure 7:
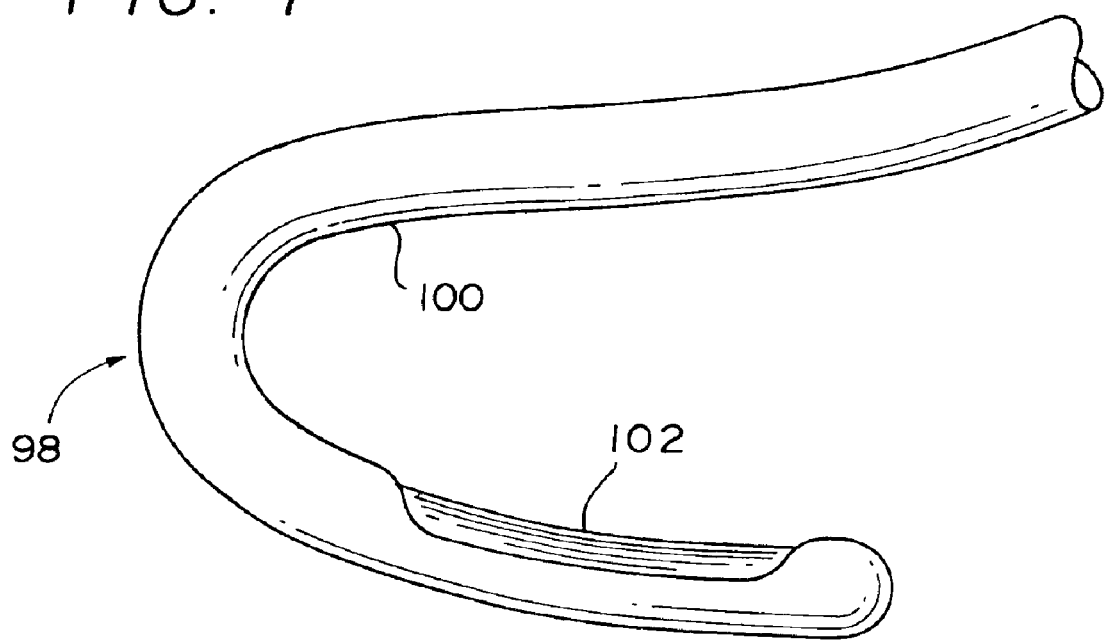
FIG. 7 is a schematic illustration of an embodiment of the cryosurgical probe having a malleable, thermally insulated main portion with a freezing portion exposed thereon.

Referring now to FIG. 7 another embodiment of the present invention is illustrated, designated generally as 98. The cryosurgical probe 98 includes an elongated shaft assembly that has malleable and thermally insulated portion 100. However, a desired freezing portion 102 is exposed thereon. This embodiment is useful for directing the cryogenic effect in a specific desired direction while avoiding damage to adjacent structures.

Figure 8:
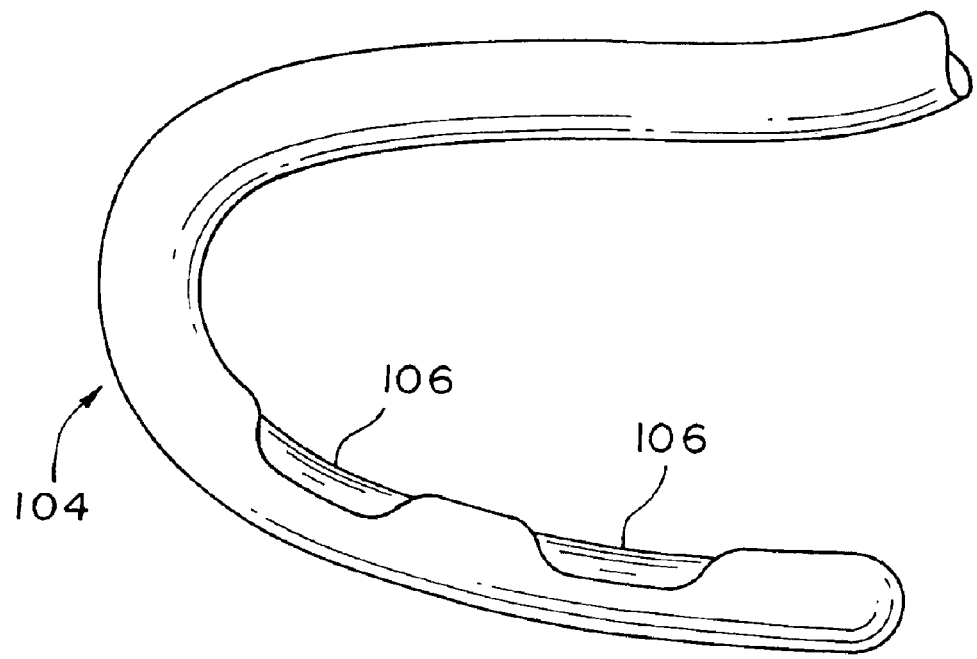
FIG. 8 illustrates the use of multiple freezing portions.

The FIG. 8 embodiment, designated generally as 104 is similar to that of FIG. 7; however, multiple freezing portions 106 are provided.

Figure 9:
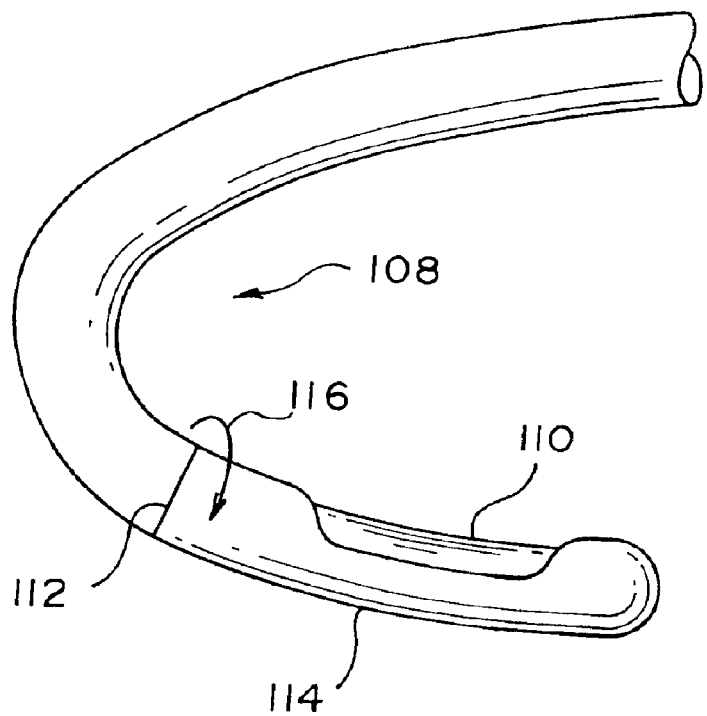
FIG. 9 illustrates the use of adjustable freezing portions.

In the embodiment illustrated in FIG. 9, designated generally as 108, the location of the freezing portion is able to be changed by providing a cut 112 in the thermal insulation, thus providing rotation of the tip portion 114, as indicated by arrow 116.

Figure 10:
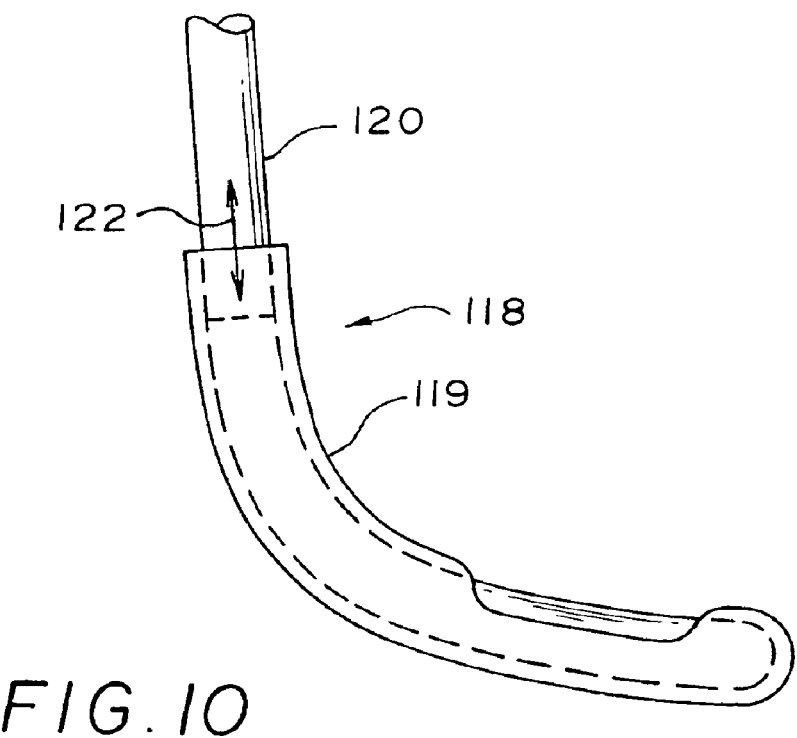
FIG. 10 illustrates the use of longitudinally adjustable freezing portions.

Referring to FIG. 10, another embodiment of the present invention is illustrated, designated generally as 118, where the thermal insulation 119 is provided with the ability for longitudinal movement along the tube 120, as indicated by arrow 122, thus allowing for the desired freezing positions.

Figure 11:
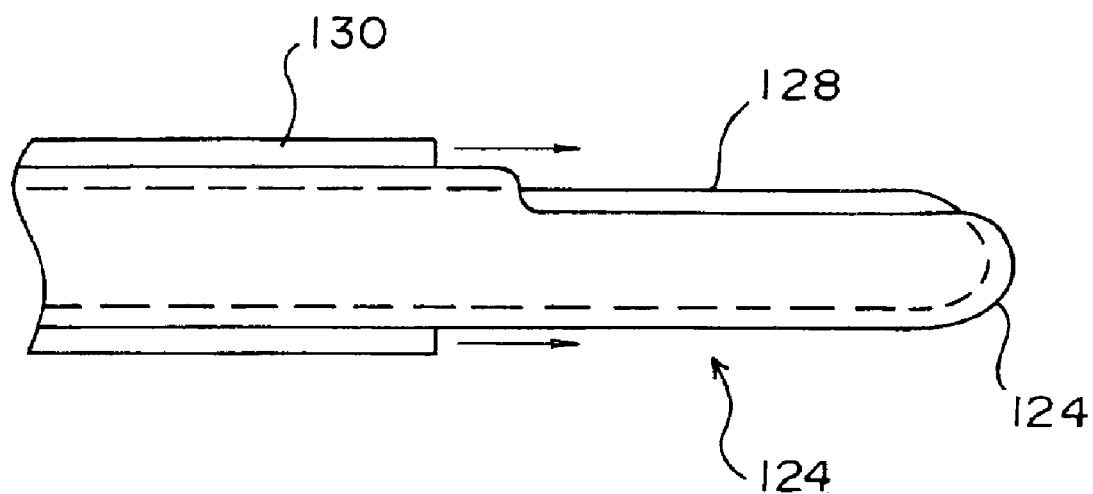
FIG. 11 is a schematic illustration of the use of multiple layers of thermal insulation to control the freeze zone.
Figure 12:
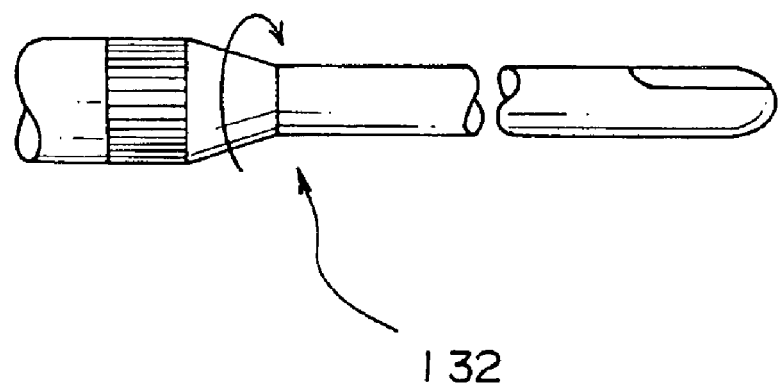
FIG. 12 is a schematic illustration of an embodiment in which a portion of the cryosurgical probe is rotatable.

Obviously, many modifications and variations of the present invention are possible in light of the above teachings. For example, FIG. 11 schematically shows how multiple layers of thermal insulation can be used to control the freeze zone. In this embodiment, designated generally as 124, an inner layer 126 of insulation about the steel shaft 128 directs freezing in one direction while a movable outer layer 130 controls the length of the freeze zone. FIG. 12 illustrates an embodiment of the present invention, designated generally as 132, in which rotation of the elongated shaft assembly or a portion of the elongated shaft assembly may be provided along its axis. It is, therefore, to be understood that within the scope of the appended claims, the invention may be practiced otherwise than as specifically described.

What is claimed and desired to be secured by Letters Patent of the United States is:

1. A malleable cryosurgical probe, comprising:
   a) a cryostat assembly, comprising:
      i) an elongated shaft assembly having at least one malleable segment thereof and a closed distal end, said shaft assembly, including:

at least one freezing portion;
at least one thermally insulated portion; and
a thermally insulating element positioned about said thermally insulated portion, said thermally insulated element being adjustably positionable to control the location, size and shape of said freezing portion,
ii) a cryostat operably associated with said elongated shaft assembly, comprising:
a cryostat inlet for receiving gas entering said cryostat;
a cryostat outlet: and,
a heat exchanger having a distal end positioned proximally from said freezing portion, said heat exchanger being positioned between said cryostat outlet and said cryostat inlet, said heat exchanger for receiving gas from said cryostat inlet and providing heat transfer between gas flowing within said cryostat and fluid exterior thereto; and,
iii) a plurality of longitudinally spaced Joule-Thomson nozzles in fluid communication with said cryostat outlet, said plurality of Joule-Thomson nozzles for expanding gas expelled therefrom, the expanded cold fluid communicating with said at least one freezing portion to provide cooling thereof; and,
b) a cryoprobe assembly, comprising:
a handle assembly for supporting said cryostat assembly, said handle assembly having an outer diameter greater than said freezing portion and said thermally insulated portion, said handle assembly, comprising:
an anchor securely connected to said cryostat assembly;
an o-ring secured to said anchor for preventing fluid from escaping through said handle assembly: and,
a handle securely connected to said anchor;
and,
a fluid supply line assembly connectable to a fluid source at one end and to said cryostat inlet at a second end, wherein said heat exchanger is positioned at a location longitudinally spaced from said at least one freezing portion and inside a volume formed by said handle assembly.

2. The malleable cryosurgical probe of claim 1, wherein said handle, comprises:
two elongated opposing handle body elements including means for securing said handle body elements to said anchor;
a handle nozzle for securing said handle body elements together at first ends thereof;
a handle barb for securing said handle body elements together at second ends thereof.

3. The malleable cryosurgical probe of claim 1, wherein said malleable segment comprises a malleable tube having a shaft enhancement element positioned thereabout.

4. The malleable cryosurgical probe of claim 3, wherein said shaft enhancement element comprises a spring coil member.

5. The malleable cryosurgical probe of claim 1, wherein said elongated shaft assembly, comprises:
a main body portion including said at least one malleable segment; and
a tip portion integrally connected to said main body portion, said tip portion having said closed distal end.

6. The malleable cryosurgical probe of claim 5, wherein said main body portion comprises an adapter segment in addtion to said malleable segment, said malleable segment being located between said adapter segment and said tip portion.

7. The malleable cryosurgical probe of claim 1, wherein said heat exchanger comprises a coiled heat exchanger.

8. The malleable cryosurgical probe of claim 1, further including a temperature measurement device connectable to a data acquisition system.

9. The malleable cryosurgical probe of claim 1 wherein said malleable segment has a minimum bend radius of 0.25 inches.

10. The malleable cryosurgical probe of claim 1 wherein said freezing portion has an outer diameter in a range between about 0.04 inches and about 0.5 inches.

11. The malleable cryosurgical probe of claim 1, wherein said malleable segment includes physical properties such that it retains its shape after bending.

12. The malleable cryosurgical probe of claim 1, wherein said thermally insulated portion has an outer diameter in a range of between about 0.04 inches and about 0.50 inches.

13. The malleable cryosurgical probe of claim 1, wherein said thermally insulated portion has an outer diameter in a range of between about 0.10 inches and about 0.15.

14. The malleable cryosurgical probe of claim 1, wherein said elongated shaft assembly has a length in a range of between about 1 inch and 20 inches.

15. The malleable cryosurgical probe of claim 1, wherein said elongated shaft assembly has an outer diameter in a range of between about 0.04 inches and about 0.5 inches.

16. The malleable cryosurgical probe of claim 1, wherein said malleable segment is formed of an annealed metal.

17. The malleable cryosurgical probe of claim 1, wherein said malleable segment is formed of annealed stainless steel.

18. The malleable cryosurgical probe of claim 1, further including a temperature measurement device positioned within said elongated shaft assembly and connectable to a data acquisition system.

19. The malleable cryosurgical probe of claim 1, wherein said elongated shaft assembly, comprises:
a rigid, thermally insulated main portion; and,
a malleable tip portion, said tip portion being said at least one malleable segment.

20. The malleable cryosurgical probe of claim 1, wherein said elongated shaft assembly, comprises:
a malleable, thermally insulated main portion being said malleable segment; and
a rigid tip portion.

21. The malleable cryosurgical probe of claim 1, wherein said elongated shaft assembly, comprises:
a malleable, thermally insulated main portion; and
a malleable tip portion.

22. The malleable cryosurgical probe of claim 1, wherein said elongated shaft assembly, comprises:
a malleable and thermally insulated portion having at least one freezing portion exposed thereon.

23. The malleable cryosurgical probe of claim 1, wherein said at least one freezing portion is malleable.

24. The malleable cryosurgical probe of claim 1, wherein at least a portion of said elongated shaft assembly is rotatable about its axis.

* * * * *